(12) United States Patent
Dejima et al.

(10) Patent No.: US 8,728,121 B2
(45) Date of Patent: May 20, 2014

(54) PUNCTURE NEEDLE AND MEDICAL PROCEDURE USING PUNCTURE NEEDLE THAT IS PERFORMED VIA NATURAL ORIFICE

(75) Inventors: Takumi Dejima, Tokyo (JP); Manabu Miyamoto, Tokyo (JP); Kiyotaka Matsuno, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 481 days.

(21) Appl. No.: 11/649,036

(22) Filed: Jan. 3, 2007

(65) Prior Publication Data
US 2007/0191886 A1    Aug. 16, 2007

Related U.S. Application Data

(63) Continuation-in-part of application No. 11/331,938, filed on Jan. 13, 2006, now abandoned.

(51) Int. Cl.
*A61B 17/06* (2006.01)

(52) U.S. Cl.
USPC ........................................................ 606/222

(58) Field of Classification Search
USPC ................................................ 606/222, 144
See application file for complete search history.

(56) References Cited

U.S. PATENT DOCUMENTS

| | | |
|---|---|---|
| 3,320,835 A | 5/1967 | Flory et al. |
| 3,670,721 A | 6/1972 | Fukami et al. |
| 3,998,216 A | 12/1976 | Hosono |
| 4,196,736 A | 4/1980 | Watanabe |
| 4,253,350 A | 3/1981 | De Tarr |
| 4,362,160 A | 12/1982 | Hiltebrandt |
| 4,499,895 A | 2/1985 | Takayama |
| 4,673,073 A | 6/1987 | Weatherby |
| 4,726,355 A | 2/1988 | Okada |
| 4,841,888 A | 6/1989 | Mills et al. |
| 5,041,129 A | 8/1991 | Hayhurst et al. |
| 5,297,536 A | 3/1994 | Wilk |
| 5,342,303 A | 8/1994 | Ghaerzadeh |
| 5,417,699 A | 5/1995 | Klein et al. |
| 5,437,665 A | 8/1995 | Munro |

(Continued)

FOREIGN PATENT DOCUMENTS

| | | |
|---|---|---|
| EP | 1 518 507 A1 | 3/2005 |
| EP | 1 602 336 A2 | 12/2005 |
| WO | WO 99/44506 | 9/1999 |
| WO | WO 2006/005075 A2 | 1/2006 |

OTHER PUBLICATIONS

U.S. Office Action dated Oct. 26, 2009.

(Continued)

*Primary Examiner* — Tuan V Nguyen
*Assistant Examiner* — Sarah Simpson
(74) *Attorney, Agent, or Firm* — Scully, Scott, Murphy & Presser, P.C.

(57) ABSTRACT

A puncture needle includes: a needle part that has a first needle part and a second needle part that are hollow, adjacent, and have resiliency; and a sheath that retractably accommodates the needle part; in which a bend part that separates distal end sides of the first needle part and the second needle part to be further apart than proximal end sides thereof is provided in at least one of the first needle part and the second needle part.

9 Claims, 22 Drawing Sheets

(56) References Cited

U.S. PATENT DOCUMENTS

| | | | |
|---|---|---|---|
| 5,458,131 | A | 10/1995 | Wilk |
| 5,591,179 | A | 1/1997 | Edelstein |
| 5,632,717 | A | 5/1997 | Yoon |
| 5,643,293 | A | 7/1997 | Kogasaka et al. |
| 5,681,260 | A | 10/1997 | Ueda et al. |
| 5,700,273 | A | 12/1997 | Buelna et al. |
| 5,792,153 | A | 8/1998 | Swain et al. |
| RE36,020 | E | 12/1998 | Moore et al. |
| 5,935,107 | A | 8/1999 | Taylor et al. |
| 5,938,668 | A | 8/1999 | Scirica et al. |
| 5,954,732 | A | 9/1999 | Hart et al. |
| 5,984,917 | A | 11/1999 | Fleischman et al. |
| 6,068,603 | A | 5/2000 | Suzuki |
| 6,071,263 | A | 6/2000 | Kirkman |
| 6,106,510 | A | 8/2000 | Lunn et al. |
| 6,245,079 | B1 | 6/2001 | Nobles et al. |
| 6,319,263 | B1 | 11/2001 | Levinson |
| 6,402,740 | B1 | 6/2002 | Ellis et al. |
| 6,491,707 | B2 * | 12/2002 | Makower et al. ............ 606/157 |
| 6,517,498 | B1 | 2/2003 | Burbank et al. |
| 6,520,214 | B1 | 2/2003 | Sugiyama et al. |
| 6,551,329 | B1 | 4/2003 | Kortenbach et al. |
| 6,638,234 | B2 | 10/2003 | Burbank et al. |
| 6,641,528 | B2 | 11/2003 | Torii |
| 6,689,130 | B2 | 2/2004 | Arai et al. |
| 6,758,848 | B2 | 7/2004 | Burbank et al. |
| 6,837,846 | B2 | 1/2005 | Jaffe et al. |
| 6,939,349 | B2 | 9/2005 | Fleischman et al. |
| 7,033,315 | B2 | 4/2006 | Smith |
| 7,118,569 | B2 | 10/2006 | Snay et al. |
| 7,201,731 | B1 | 4/2007 | Lundquist et al. |
| 7,250,027 | B2 | 7/2007 | Barry |
| 7,455,675 | B2 * | 11/2008 | Schur et al. ............ 606/139 |
| 7,575,568 | B2 | 8/2009 | Holman et al. |
| 7,578,786 | B2 | 8/2009 | Boulais et al. |
| 7,828,790 | B2 | 11/2010 | Griffin |
| 7,846,179 | B2 * | 12/2010 | Belef et al. ............ 606/222 |
| 2001/0049497 | A1 | 12/2001 | Kalloo et al. |
| 2002/0022851 | A1 | 2/2002 | Kalloo et al. |
| 2002/0111534 | A1 * | 8/2002 | Suzuki et al. ............ 600/102 |
| 2002/0165589 | A1 | 11/2002 | Imran et al. |
| 2003/0083550 | A1 | 5/2003 | Miyagi |
| 2003/0130560 | A1 | 7/2003 | Suzuki et al. |
| 2003/0229296 | A1 | 12/2003 | Ishikawa et al. |
| 2003/0236535 | A1 | 12/2003 | Onuki et al. |
| 2004/0050395 | A1 | 3/2004 | Ueda et al. |
| 2004/0059350 | A1 * | 3/2004 | Gordon et al. ............ 606/144 |
| 2004/0127917 | A1 * | 7/2004 | Ginn ............ 606/151 |
| 2004/0193016 | A1 | 9/2004 | Root et al. |
| 2004/0231683 | A1 | 11/2004 | Eng et al. |
| 2004/0249392 | A1 | 12/2004 | Mikkaichi et al. |
| 2005/0107663 | A1 | 5/2005 | Sadaat et al. |
| 2005/0125021 | A1 | 6/2005 | Nance et al. |
| 2005/0137453 | A1 | 6/2005 | Ouchi et al. |
| 2005/0165272 | A1 | 7/2005 | Okada et al. |
| 2005/0236277 | A9 | 10/2005 | Imran et al. |
| 2005/0250986 | A1 | 11/2005 | Rothe et al. |
| 2005/0288688 | A1 | 12/2005 | Sakamoto et al. |

OTHER PUBLICATIONS

U.S. Office Action dated Dec. 3, 2009 received in related U.S. Appl. No. 11/358,257.
U.S. Office Action dated Jun. 8, 2010 received in related U.S. Appl. No. 11/435,182.
European Search Report for European Patent Application No. 10010338.1-1526, mailed Nov. 2, 2010.
Office Action mailed Jan. 10, 2011 in related U.S. Appl. No. 12/103,441.
United States Office Action mailed Jan. 31, 2011 in related U.S. Appl. No. 11/649,099.
U.S. Office Action mailed Feb. 14, 2011 in related U.S. Appl. No. 12/103,439.
U.S. Office Action issued Jul. 22, 2010 in related U.S. Appl. No. 12/103,439.
U.S. Office Action issued Jul. 22, 2010 in related U.S. Appl. No. 12/103,441.
U.S. Office Action mailed on May 26, 2011 in related U.S. Appl. No. 12/103,441.
U.S. Office Action mailed on Mar. 30, 2010 in related U.S. Appl. No. 11/331,938.
U.S. Office Action, mailed on Jan. 17, 2013 in related U.S. Appl. No. 11/435,182.
U.S. Office Action, mailed on Mar. 29, 2012 in related U.S. Appl. No. 11/435,182.
U.S. Office Action, mailed on Jul. 3, 2012 in related U.S. Appl. No. 12/958,867.
U.S. Office Action mailed on Jul. 12, 2011 in related U.S. Appl. No. 11/435,182.
U.S. Office Action mailed on Jul. 18, 2011 in related U.S. Appl. No. 12/103,439.
U.S. Office Action mailed on Jul. 21, 2011 in related U.S. Appl. No. 11/649,099.
U.S. Office Action, mailed on Sep. 7, 2011 in U.S. Appl. No. 11/360,198.
U.S. Office Action, mailed on Aug. 27, 2012 in related U.S. Appl. No. 11/649,099.
U.S. Office Action, mailed on Sep. 13, 2012 in related U.S. Appl. No. 12/103,439.
U.S. Office Action dated Dec. 2, 2013 in related U.S. Appl. No. 12/103,441.

* cited by examiner

PUNCTURE NEEDLE AND MEDICAL PROCEDURE USING PUNCTURE NEEDLE THAT IS PERFORMED VIA NATURAL ORIFICE

Priority is claimed on U.S. patent application Ser. No. 11/331,938, filed Jan. 13, 2006, the content of which is incorporated herein by reference. This application is a continuation-in-part of U.S. patent application Ser. No. 11/331,938.

BACKGROUND OF THE INVENTION

Field of the Invention

The present invention relates to a puncture needle and medical procedure using the puncture needle that is performed via a natural orifice.

DESCRIPTION OF RELATED ART

Laparoscopic operations are known in which, in performing a medical procedure of observing, treating, etc. an organ of the human body, instead of incising the abdominal wall widely, a plurality of orifices are opened in the abdominal wall and procedures are performed upon inserting a laparoscope, forceps, and other treatment instruments into the orifices. Such procedure provides the benefit of lessening the burden placed on the patient because only small orifices need to be opened in the abdominal wall.

In recent years, methods of performing procedures upon inserting a flexible endoscope via the mouth, nose, anus, or other natural orifice of the patient have been proposed as methods of further reducing the burden on the patient. An example of such procedures is disclosed in U.S. Pat. No. 5,458,131.

With this method, a flexible endoscope is inserted from the mouth of a patient, an opening is formed in the stomach wall, and a distal end part of the endoscope is fed into the abdominal cavity from the opening. Then while using the endoscope as a device for observing the interior of the abdominal cavity, desired procedures are performed inside the abdominal cavity using a treatment instrument inserted through the endoscope or a treatment instrument inserted from another opening.

SUMMARY OF THE INVENTION

An object of this invention is to provide a puncture needle that can more readily suture incised tissue in performing a medical procedure using an endoscope, and a medical procedure using the puncture needle that is performed via a natural orifice.

A puncture needle according to a first aspect of this invention includes: a needle part that has a first needle part and a second needle part that are hollow, adjacent, and have resiliency; and a sheath that accommodates the needle part to freely protrude and retreat; in which a bend part that separates distal end sides of the first needle part and the second needle part to be further apart than proximal end sides thereof is provided in at least one of the first needle part and the second needle part.

A medical procedure through a natural orifice according to a second aspect of this invention includes: inserting a device that extends in an axial direction into a lumen disposed in an insertion part of an overtube and inserting the insertion part into a hollow organ through a natural orifice of a subject; guiding the insertion part to an incision target site while using an observation device to observe the incision target site; inserting the puncture needle according to the first aspect of this invention via the device insertion part up to the incision target site and simultaneously placing placing members disposed on the puncture needle at a plurality of locations; forming an opening at the incision target site; introducing at least one of an operative device and the overtube into an abdominal cavity via the opening; and suturing the opening using the placing member.

DETAILED DESCRIPTION OF THE INVENTION

Embodiments according to the present invention will now be described in detail below. In the following description, components that are the same shall be provided with the same numeric symbol and redundant description shall be omitted.

Figure 1:
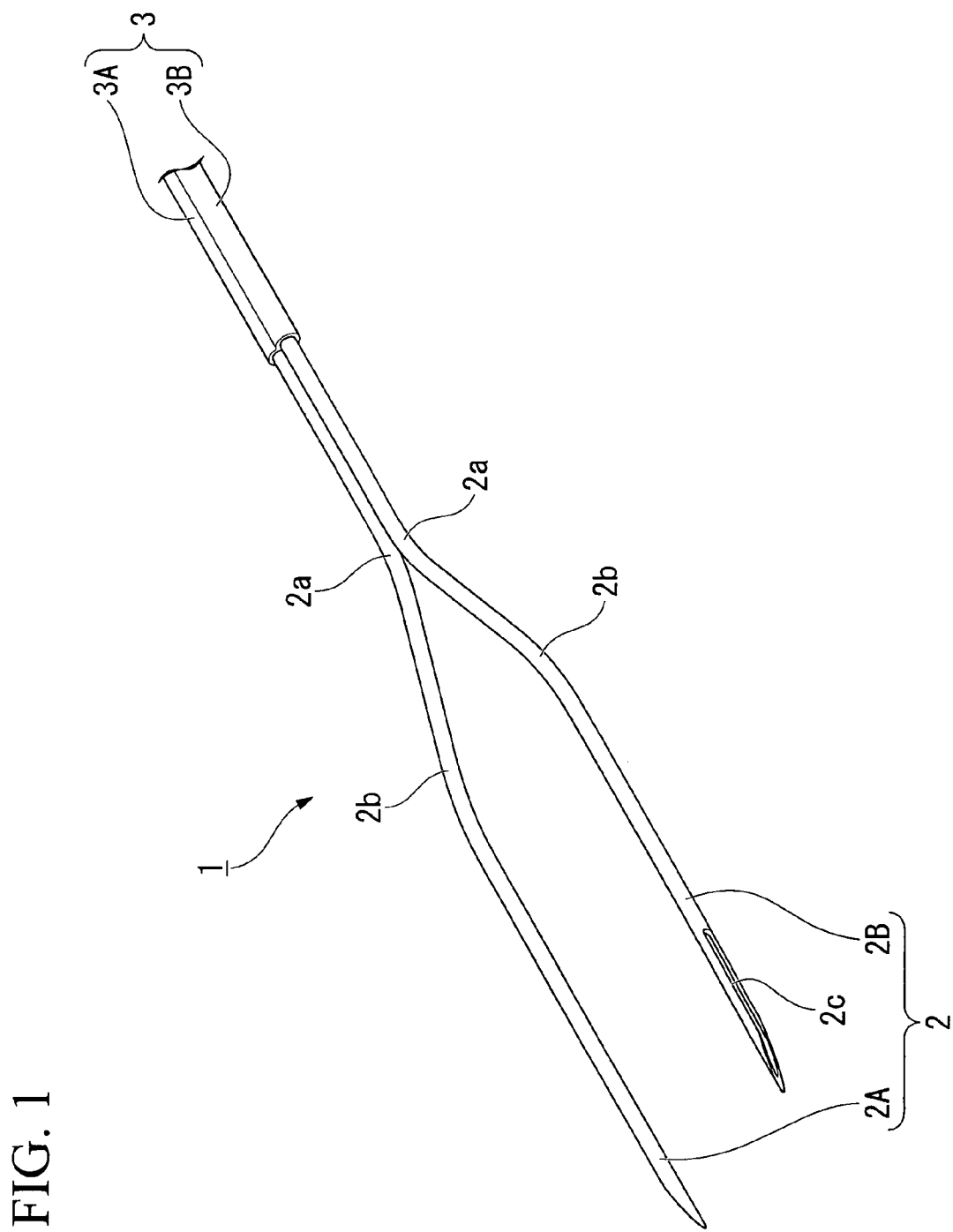
FIG. 1 is a view showing the principal portions of the puncture needle according to one embodiment.
Figure 2:
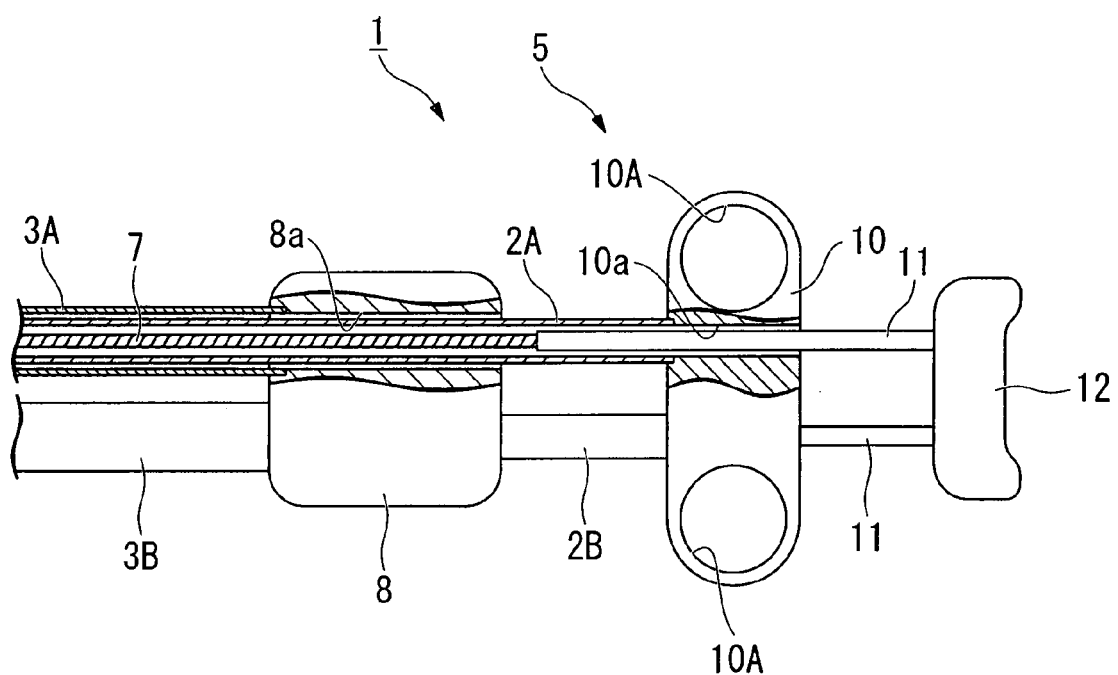
FIG. 2 is a view showing the manipulating part of the puncture needle according to the embodiment.

As shown in FIG. 1 and FIG. 2, a puncture needle 1 according to the present embodiment includes: a needle part 2 that has a first needle part 2A and a second needle part 2B that are hollow, adjacent, and have resiliency; and a sheath 3 that accommodates the first needle part 2A and the second needle part 2B to freely protrude and retreat; and a needle manipulating part 5 that extends and retracts the needle parts 2A and 2B with respect to the sheath 3.

The first needle part 2A and the second needle part 2B are each provided with a bend part 2a that separates a distal end side of the first needle part 2A and the second needle part 2B to be further apart than a proximal end side thereof. Further to the distal end side than the bend part 2a of the first needle part 2A and the second needle part 2B is also provided an alignment part 2b that disposes the distal end sides of the first needle part 2A and the second needle part 2B to be mutually parallel. A slit 2c through which a suture 6C described below passes is formed at the distal end of the first needle part 2A and the second needle part 2B. The bend part 2a and the alignment part 2b resiliently deform to be accommodated in the sheath 3 when accommodating the needle parts 2A and 2B in the sheath 3.

Figure 3:
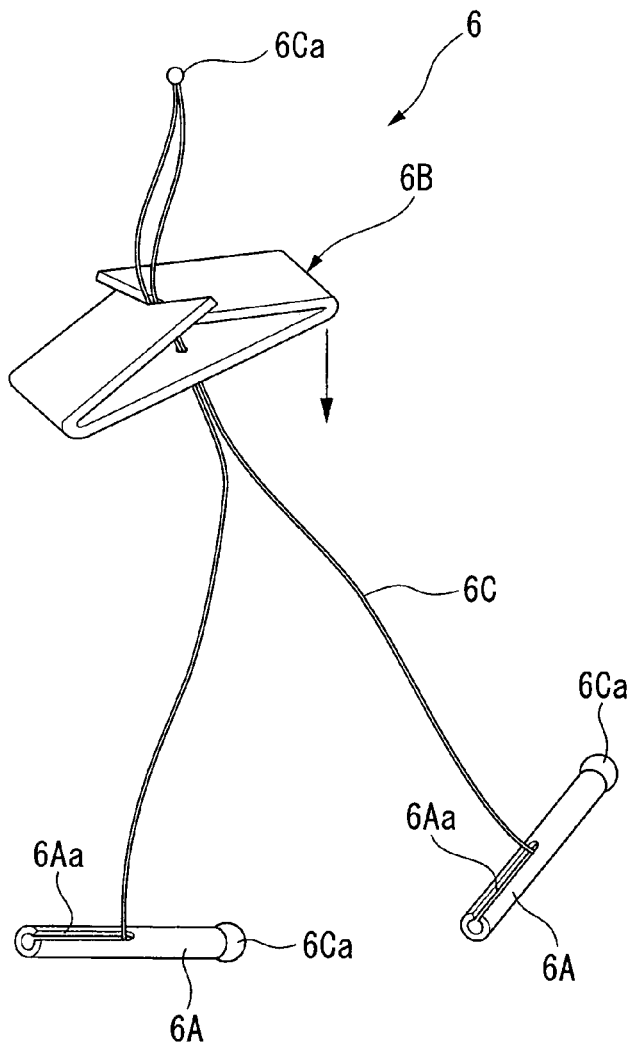
FIG. 3 is an overall view of the double T-bars used in the embodiment.
Figure 4:
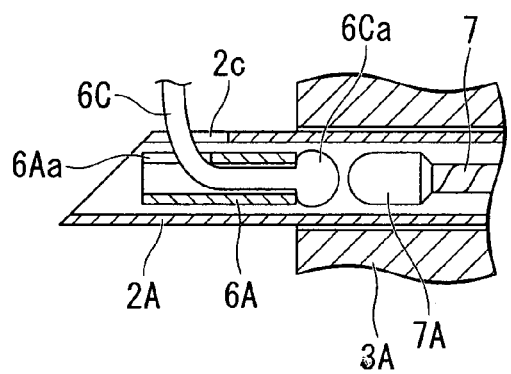
FIG. 4 is a sectional view of a state in which the double T-bars are fitted into a puncture needle according to the embodiment.

Two anchors 6A of double T-bars (placing members) 6, shown in FIG. 3, are respectively held inside the respective needle parts 2A and 2B as shown in FIG. 4. The double T-bars 6 have two sutures (wires) 6C, one end side of each being passed through a substantially triangular stopper 6B. At one end, the sutures 6C are bound together to form a large diameter part 6Ca. Each of the other ends of the sutures 6C is fixed to the anchors 6A. Each anchor 6A has a cylindrical shape with a slit formed at an end, and the suture 6C is inserted in the longitudinal direction of the interior of anchor 6A through the slit. The large diameter part 6Ca that has greater diameter than that of the anchor 6A is formed at the other end of the suture 6C. The stopper 6B has a hole, through which the sutures 6C are passed, at a center in the longitudinal direction of an elongated, thin plate member. The respective ends in the longitudinal direction of the stopper 6B are folded obliquely and sandwich the sutures 6C. The respective ends in the longitudinal direction of the stopper 6B are cut to notches of triangular shape. With the stopper 6B, the respective ends are folded back obliquely so that the notches intersect and thereby sandwich the sutures 6C. The sutures 6C thus do not fall off from between the ends. When the large diameter part 6Ca of the sutures 6C is pulled in a direction away from the stopper 6B, the respective end parts of the stopper 6B spread apart slightly. The stopper 6B thus allows movement of the sutures 6C in this direction. Meanwhile, when a large diameter part 6Ca at the anchor 6A side of a suture 6C is pulled, a tendency for the suture 6C to move in the direction indicated by the arrow in FIG. 3 arises. However, since the respective ends of the stopper 6B close and grasp the sutures 6C in this process, the suture 6C does not move. As shown in FIG. 4, a pusher 7 is movably disposed in advancing and retracting directions in the interior of the respective needle parts 2A and 2B. A rigid, pushing member 7A is disposed at a distal end of the pusher 7.

The sheath 3 is provided with a first sheath 3A that accommodates the first needle part 2A to freely protrude and retreat and a second sheath 3B that accommodates the second needle part 2B to freely protrude and retreat. The first sheath 3A and the second sheath 3B are disposed to be parallel, with the distal end sides thereof connected so as to be integrated. Here, the sheath 3 is of a material and size that, when housing the needle part 2 therein, the first needle part 2A and the second needle part 2B extend and deform to be accommodated in the sheath 3 by the resilient deformation of the bend parts 2a and the alignment parts 2b.

The needle manipulating part 5 includes a sheath holding part 8 connected to the proximal ends of the first sheath 3A and the second sheath 3B; a needle manipulating handle 10 connected to proximal ends of the two needle parts 2A and 2B that have been passed in a manner enabling advancing and retracting through through-holes 8a formed in the sheath holding part 8; and a pusher connection part 12 that connects end portions of rod-like, rigid parts 11, which are passed in a manner enabling advancing and retracting through throughholes 10a formed in the needle manipulating handle 10 and are connected to proximal ends of the two pushers 7, to each other. The needle manipulating handle 10 is provided with finger rings 10A. Each of the needle manipulating handle 10 and the pusher connection part 12 may be divided into two parts so as to enable the first needle part 2A and the second needle part 2B and the two pushers 7 to be manipulated independently of each other.

Figure 5:
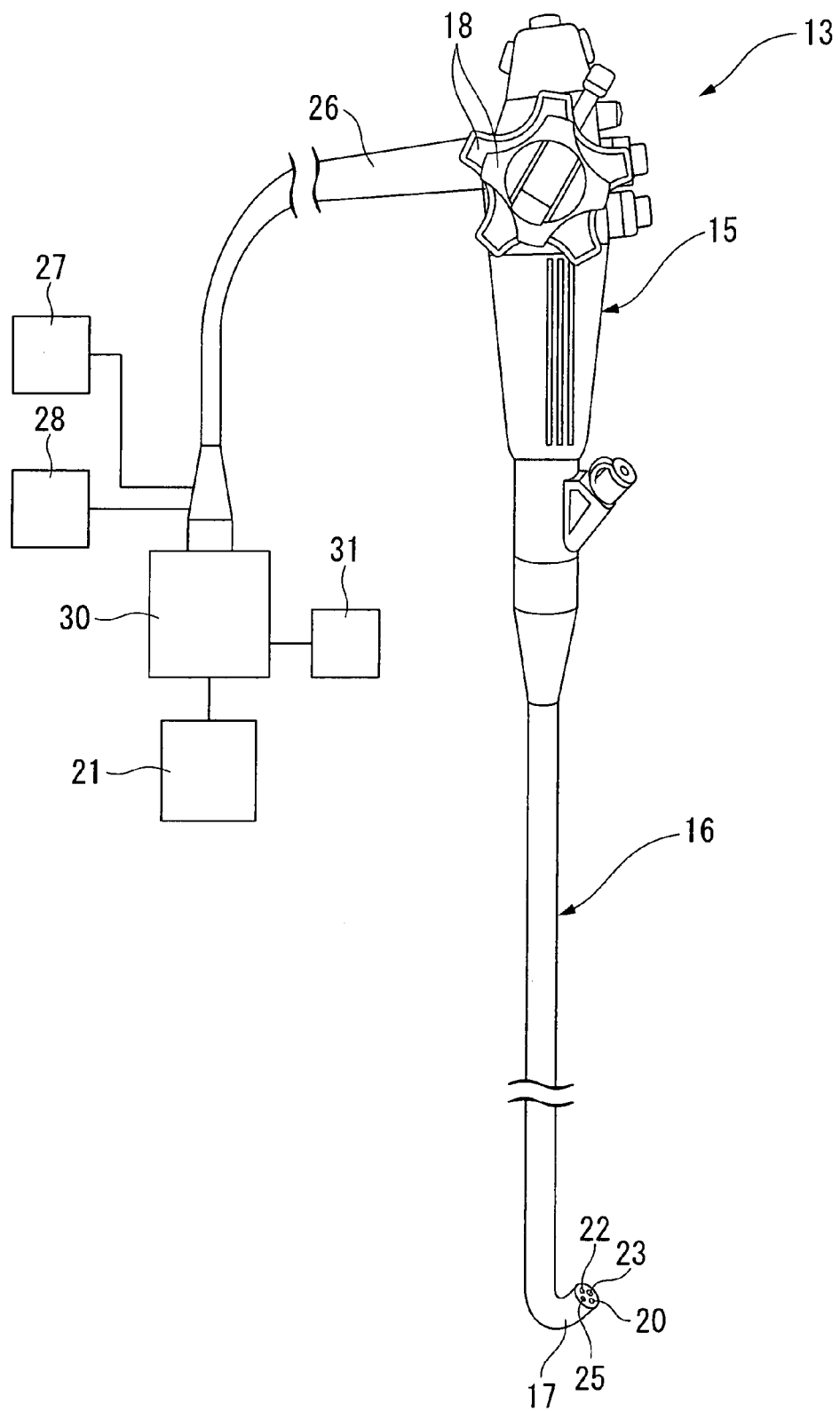
FIG. 5 is an overall schematic view of an endoscope as an example of a device used for the puncture needle according to the embodiment.

The puncture needle 1 is used for example with a flexible endoscope 13 shown in FIG. 5. This endoscope 13 consists of an endoscope inserting part 16, which is elongated and has flexibility to be inserted into a patient's body, that extends outward from an endoscope manipulating part 15 manipulated by an operator. An endoscope distal end part 17 of the endoscope inserting part 16 can be bended by manipulating an angle knob 18 disposed at the endoscope manipulating part 15. At the endoscope distal end part 17 are disposed an objective lens 20, a distal end face of an optical fiber 22 that guides light from a light source device 21 disposed outside the body, and distal end openings of treatment instrument insertion channels 23 and 25. The treatment instrument insertion channels 23 and 25 are ducts for inserting and removing a treatment instrument. Moreover, the treatment instrument insertion channel 23 is connected via a universal cable 26 to an air/water feeding device 27 or a suction device 28 disposed outside the body. The treatment instrument insertion channel 25 is disposed at a position of six o'clock to eight o'clock of the endoscope inserting part 16.

An observation image inputted into the objective lens 20 is displayed on a monitor 31 via a control unit 30.

Figure 6:
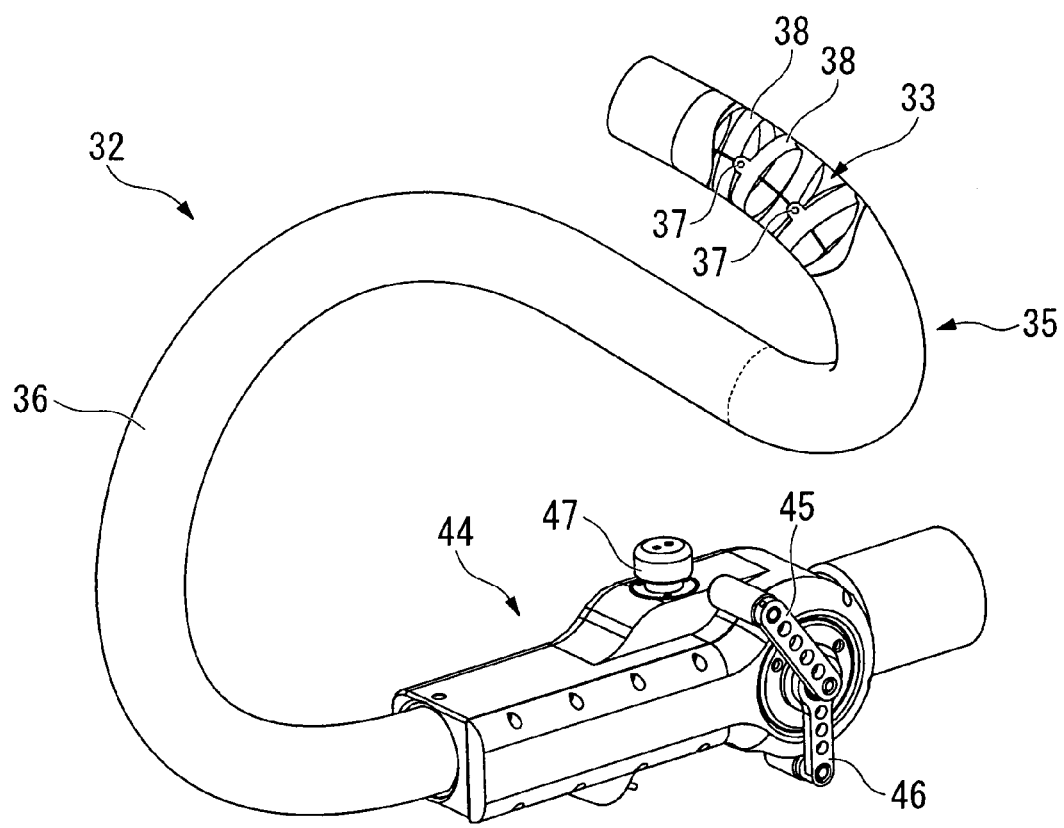
FIG. 6 is an overall schematic view of the overtube used with the puncture needle according to the embodiment.

Moreover, an overtube 32 such as shown in FIG. 6 is used as a guide tube when inserting the endocope 13 into a body. The overtube 32 includes an insertion part 36 that is inserted into a stomach or other hollow organ or abdominal cavity, etc., of a patient (subject) and has a lumen 33, through which the endoscope inserting part 16 is removably inserted, and a bending part 35 that bends the distal end side of the lumen 33.

The bending part 35 is disposed on the distal end side of the insertion part 36 and consists of a plurality of ring-shaped joint rings 38 that are mutually connected via connection shafts 37 along the lumen 33 to freely move.

A proximal handle 44 having a larger diameter than the insertion part 5, is disposed at the proximal end of the insertion part 36 of the overtube 32. The proximal handle 44 includes a bending lever 45, a bending lock lever 46, and an endoscope lock button 47. The bending lever 45 is connected to the proximal ends of the bending wires that connect the joint rings 38 for performing bending manipulation of the bending part 35. The bending lock lever 46 is used for fixing the position of the bending lever 45 at an arbitrary position. The endoscope lock button 47 is used for fixing the endoscope 13 with respect to the lumen 33 upon insertion of the endoscope 13 through the lumen 33.

When the endoscope 13 must be fixed to the insertion part 5 upon being inserted through the interior, pressing the endoscope lock button 47 inward in the radial direction presses and fixes the endoscope 13 in a relative manner by a frictional force. The endoscope lock button 47 may be arranged so as to oppositely release the frictional force when pressed.

Figure 7:
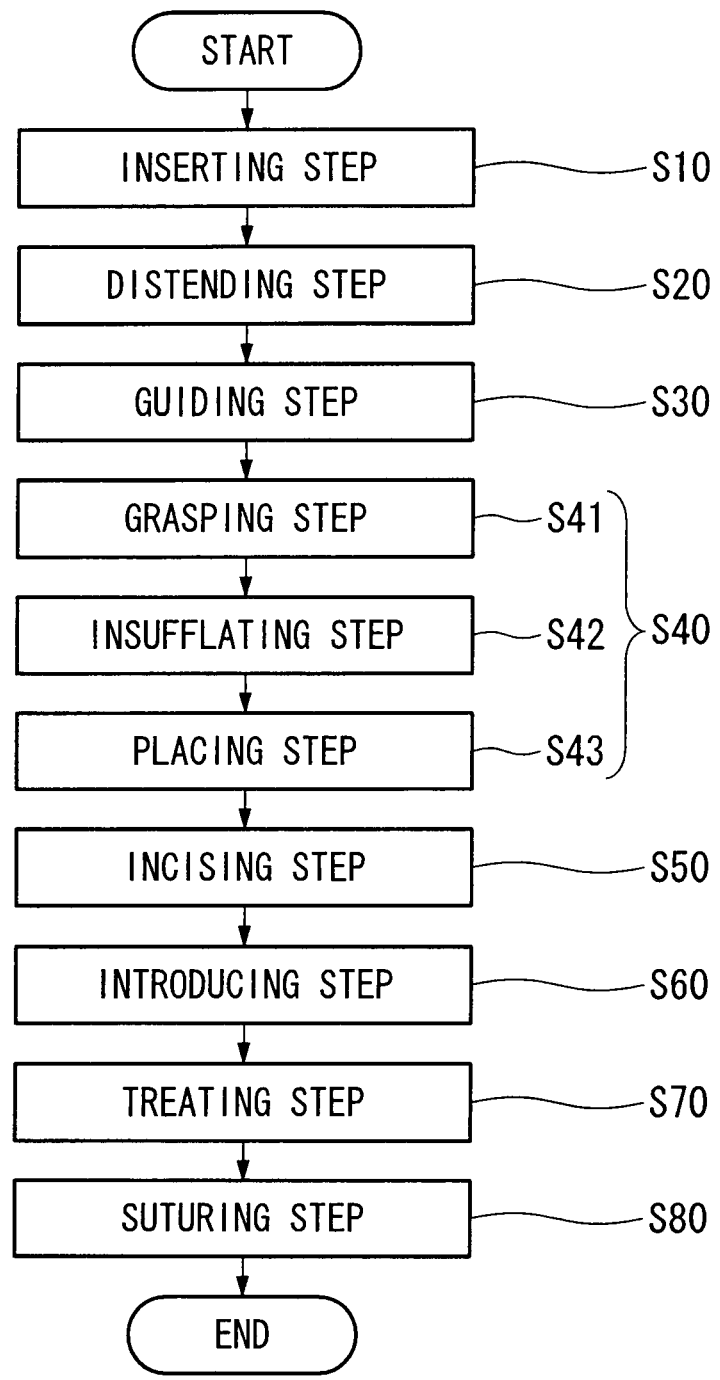
FIG. 7 is a flowchart of a medical procedure according to the embodiment.

Actions of the present embodiment shall now be described in line with a medical procedure performed via a natural orifice as shown by the flow chart of FIG. 7. In the following description, it shall be deemed that an incision target site is located on an anterior wall of a stomach, and a surgical procedure of inserting the endoscope 13 into the stomach from a mouth (natural orifice) of a patient (subject) and performing treatment upon forming an opening in the stomach wall and inserting the endoscope inserting part 16 into an abdominal cavity shall be described. Also, though in the embodiment described below, the endoscope 13 is introduced into the body from the mouth of the patient and made to approach the abdominal cavity upon forming the opening in the anterior wall of the stomach, the natural orifice from which the endoscope 13 is introduced is not restricted to the mouth and may be another natural orifice, such as the anus, nose, etc. Furthermore, though the forming of the opening in the anterior wall of the stomach is desirable, this invention is not restricted thereto, and an opening may be formed on the wall of another hollow organ (hollow organ) into which a device is introduced via a natural orifice, such as another area of the stomach, the esophagus, small intestine, or large intestine.

The medical procedure performed via a natural orifice according to the present embodiment consists of an inserting step (S10) of inserting the endoscope inserting part 16 through the lumen 33 that is disposed in the insertion part 36 of the overtube 32 and inserting the insertion part 36 of the overtube 32 into the stomach (hollow organ) from the mouth of the patient; a distending step (S20) in which air is supplied to inflate the stomach; a guiding step (S30) of guiding the insertion part to the incision target site while checking the incision target site using the endoscope 13; a needle moving step (S40) of inserting the puncture needle 1 to the incision target site via the endoscope inserting part 16 and placing the double T-bars 6 disposed on the puncture needle 1 at two locations simultaneously; an incising step (S50) of providing an opening in the incision target site; an introducing step (S60) of introducing at least one of the endoscope inserting part 16 and the insertion part 36 of the overtube 32 into the abdominal cavity through the opening; a treating step (S70) of performing a predetermined treatment in the abdominal cavity; and a suturing step (S80) of suturing the opening using the double T-bars 6. Contents of each of the steps are explained below.

Figure 8:
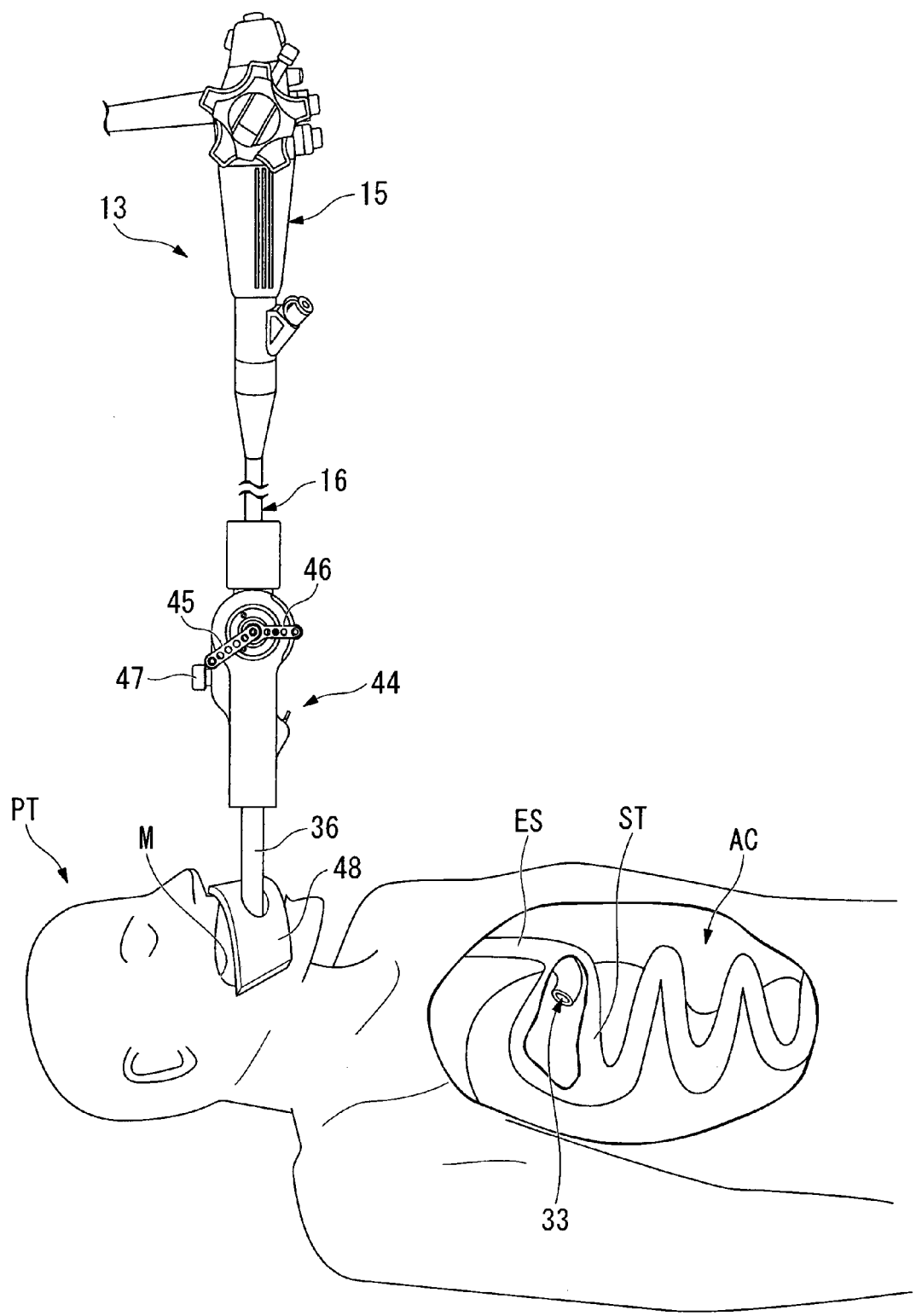
FIG. 8 is a view for describing a state of inserting the endoscope into the overtube in the medical procedure according to the embodiment.

First, as shown in FIG. 8, with the patient PT being made to lie in a supine position, the inserting step (S10) of inserting the endoscope inserting part 16 through the lumen 33 in the insertion part 36 of the overtube 32 and inserting the insertion part 36 of the overtube 32 and the endoscope inserting part 16 into the stomach ST from the mouth M of the patient PT while observing the interior of the body cavity by means of an endoscopic image is performed. A mouthpiece 48 is fitted onto the mouth of the patient PT and the overtube 32 and the endoscope 13 are inserted, with the endoscope inserting part 16 being inserted through the interior of the lumen 33, into the esophagus ES from the mouthpiece 48.

Next, in the distending step (S20), air is supplied from the air/water feeding device 27 via the treatment instrument insertion channel 23 of the endoscope inserting part 16 to inflate the stomach ST.

The guiding step (S30) of guiding the insertion part 36 of the overtube 32 to the incision target site T while checking the incision target site T using the endoscope 13, which is also an observation device, is then performed. First, after inserting the endoscope inserting part 16 of the endoscope 13 into the stomach ST, the angle knob 18 is manipulated to bring the distal end of the endoscope inserting part 16 close to the incision target site T while observing the interior of the stomach ST via the objective lens 20, disposed at the endoscope inserting part 16. Then with the incision target site T being specified, the endoscope inserting part 16 is used as a guide to push the insertion part 36 of the overtube 32 and bring the distal end close to the incision target site T.

The needle moving step (S40) of making the needle part 2 of the puncture needle 1 puncture the stomach wall SW and placing the double T-bars 6 is then performed.

Figure 9:
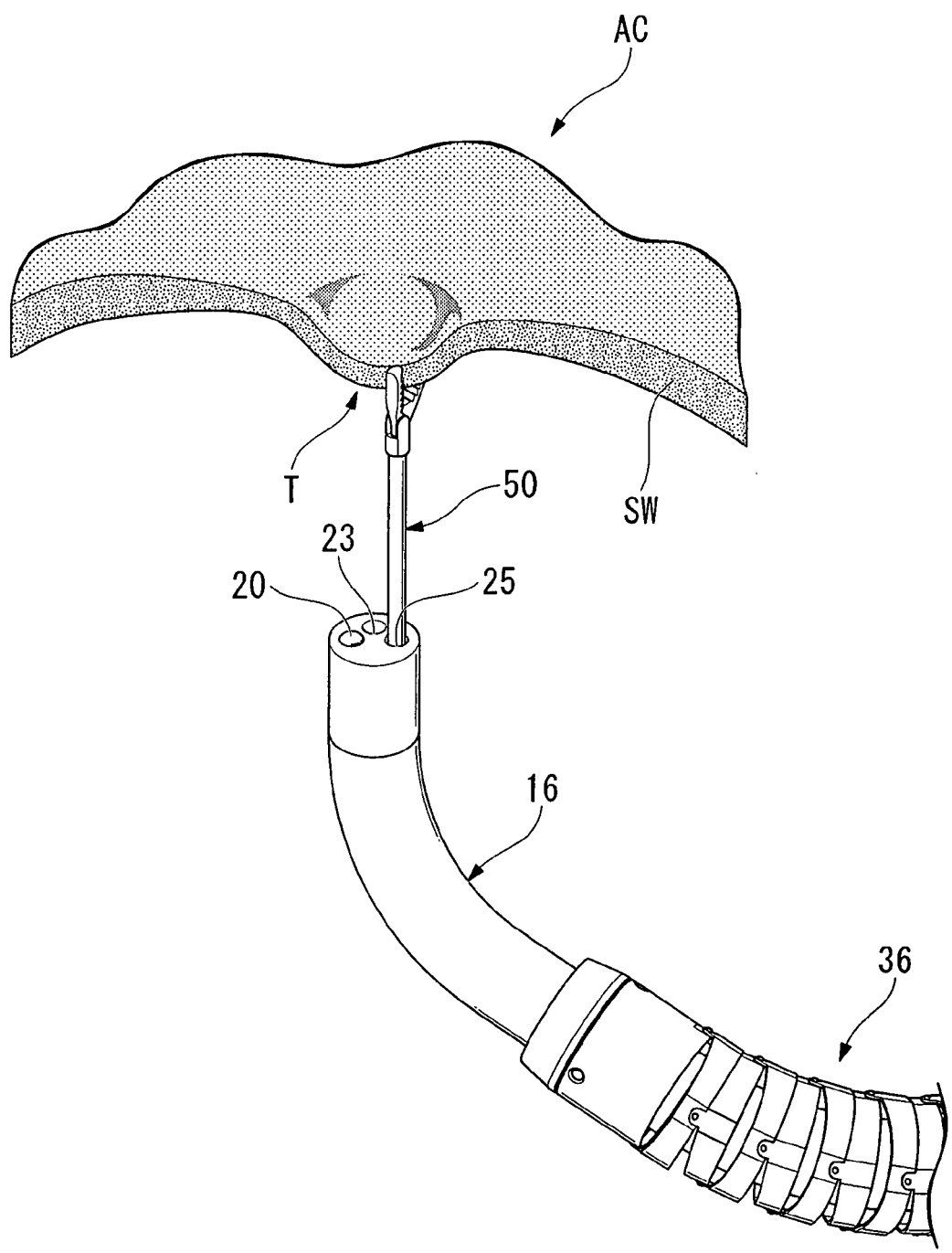
FIG. 9 is a view for describing a state of grasping an incision target site with grasping forceps in the medical procedure according to the embodiment.

First, in a grasping step (S41), as shown in FIG. 9, the endoscope inserting part 16 is protruded from the distal end of the insertion part 36 of the overtube 32, and grasping forceps 50 inserted in the treatment instrument insertion channel 25 are further protruded near the incision target site T to grasp the stomach wall SW including the incision target site T. Then, by pulling the grasping forceps 50 into the treatment instrument insertion channel 25, a sufficient space is thereby secured in the abdominal cavity AC on the outer side of the stomach wall SW by making the stomach wall SW concave.

Figure 10:
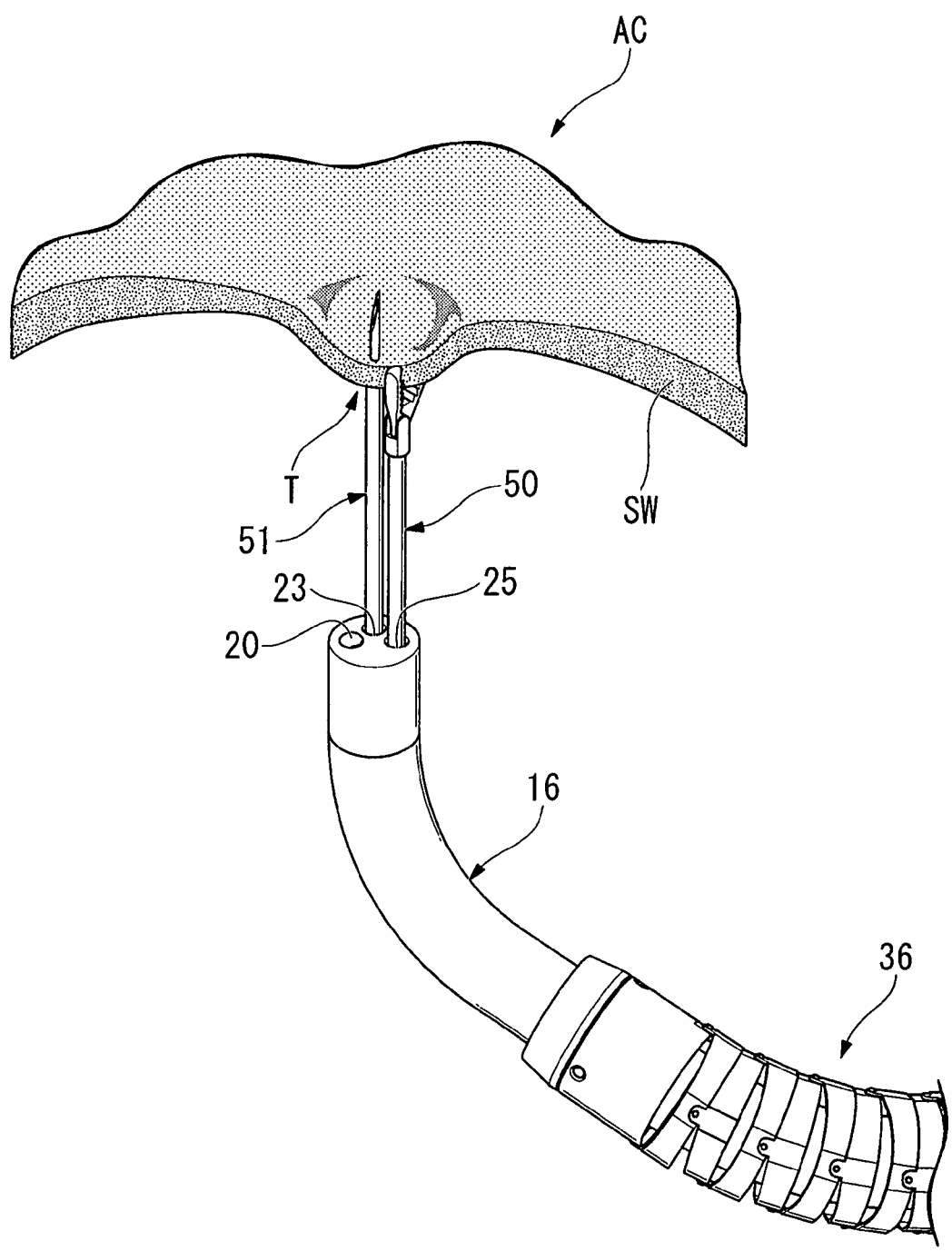
FIG. 10 is a view for describing a state of insufflating by feeding air from an injection needle in the medical procedure according to the embodiment.

An abdominal cavity insufflating step (S42) is then performed. First, an injection needle 51 connected to the air/water feeding device not shown is inserted through the treatment instrument insertion channel 23 of the endoscope 13. A distal end of the injection needle 51 is then protruded from the distal end, and as shown in FIG. 10, pierced through the stomach wall SW pulled by the grasping forceps 50 and inserted up to the abdominal cavity AC. Because the injection needle 51 pierces with the stomach SW wall being pulled in and a space being secured with the abdominal wall not shown, just the stomach wall SW can be punctured reliably. Air is then fed into the abdominal cavity AC via the injection needle 51 so that the stomach ST and the abdominal wall separate.

The injection needle 51 preferably has a needle length of approximately 12 mm and more preferably has a bendable distal end to enable piercing of the center of the pulled stomach wall. In this case, a bended injection needle has a bending tendency at a distal end and has a bending wire (not shown) that passes from the distal end toward a proximal side in an inward radial direction of the bending tendency. Here, since the treatment instrument insertion channel 23 of the endoscope 13 is disposed at a position of six o'clock to eight o'clock of the endoscope inserting part 16, the incision site is approached from an upward angle in incising the anterior stomach wall SW of the stomach ST that is preferable as the incision site. Accordingly, since the bending tendency faces the center of the bending wire following the bended state of the insertion part 36 of the overtube 32, the center of the stomach wall can be punctured reliably by pulling the bending wire toward the proximal side. In the process of feeding air, the interior of the abdominal cavity AC may be maintained at an appropriate pressure by monitoring and automatic control of the feed air pressure.

A placing step (S43) is then performed.

First, the needle manipulating handle 10 is advanced in the direction of the sheath holding part 8 while holding the sheath holding part 8 to make at least the bend part 2*a* of the first needle part 2A and the second needle part 2B protrude from the distal end of the first sheath 3A and the second sheath 3B until an exposed position. Then, the anchors 6A of the double T-bars 6 are inserted in the first needle part 2A and the second needle part 2B.

Figure 11:
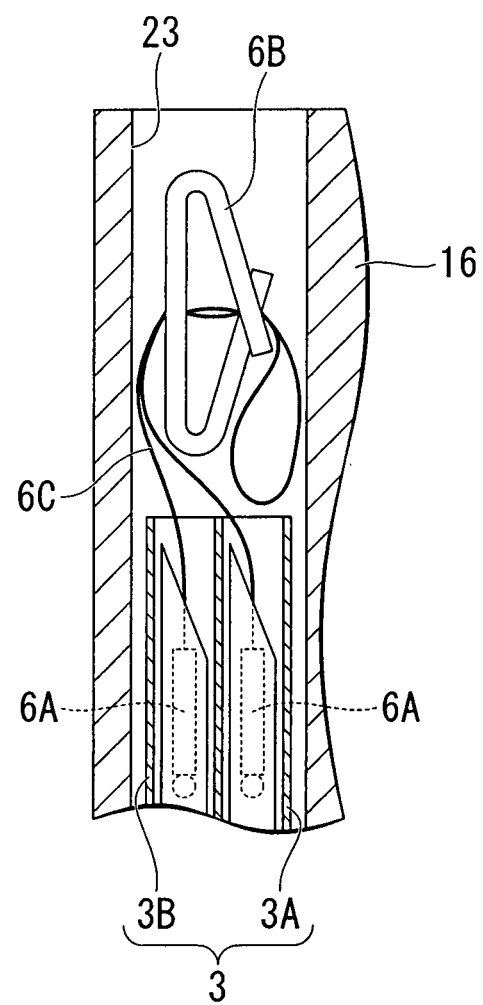
FIG. 11 is a view for describing a state of the puncture needle accommodated in the treatment instrument insertion channel in the medical procedure according to the embodiment.

Next, the needle manipulating handle 10 is again retracted toward the proximal side, and as shown in FIG. 11, the first needle part 2A and the second needle part 2B are respectively plunged into the first sheath 3A and the second sheath 3B. At this time, the stopper 6B side of the double T-bars 6 is also in a state of insertion in the sheath 3. The puncture needle 1 in this state is inserted in the treatment instrument insertion channel 23 instead of the injection needle 51.

Figure 12:
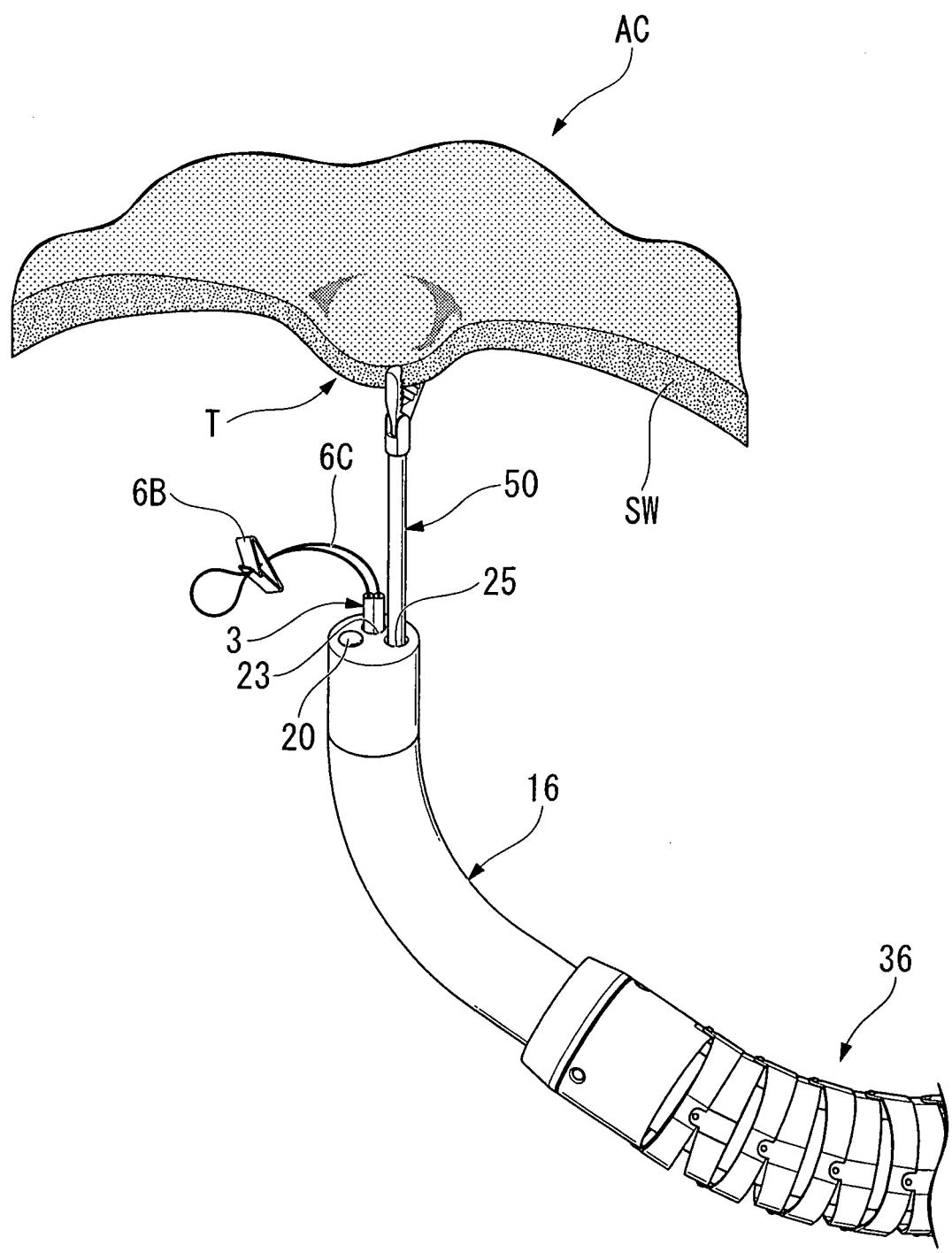
FIG. 12 is a view for describing a state of protruding the puncture needle from the treatment instrument insertion channel in the medical procedure according to the embodiment.
Figure 13:
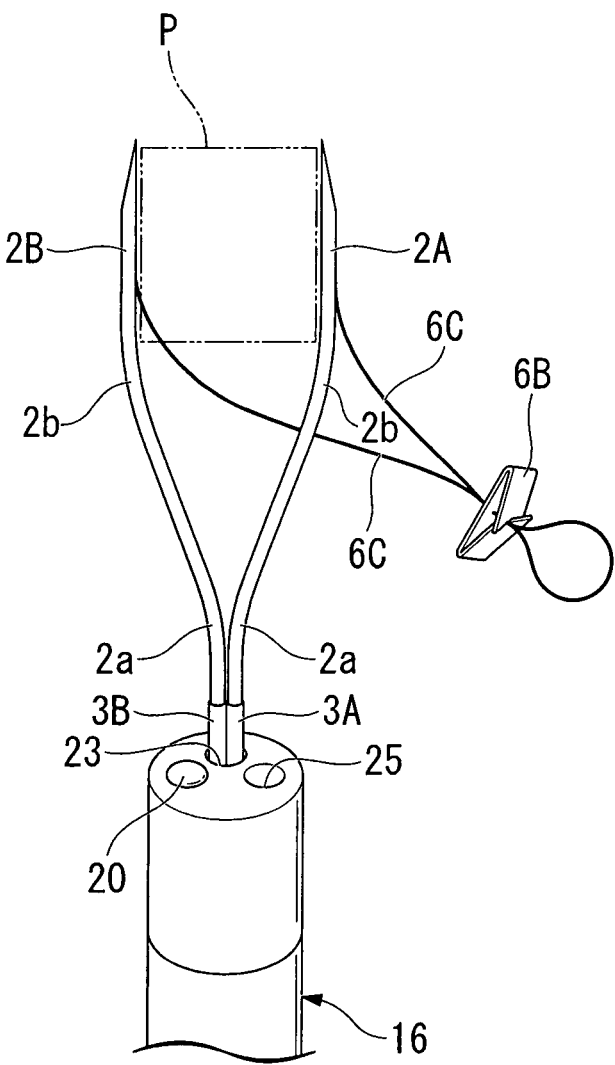
FIG. 13 is a view for describing a state of the double T-bars being retained in the puncture needle in the medical procedure according to the embodiment.

As shown in FIG. 12, the distal end of the sheath 3 is protruded from the treatment instrument insertion channel 23 to be disposed near the stomach wall SW. Moreover, the needle manipulating handle 10 is advanced in the direction of the sheath holding part 8, and as shown in FIG. 13, the distal end sides further than at least the bend parts 2*a* of the first needle part 2A and the second needle part 2B are protruded from the distal end of the sheath 3. At this time, the distal end sides further than the alignment parts 2*b* are extended in parallel separated by a predetermined distance. At this time, the distal end sides of the first needle part 2A and the second needle part 2B are disposed in a stable state on one plane P by the needle manipulating handle 10 and the sheath holding part 8.

Figure 14:
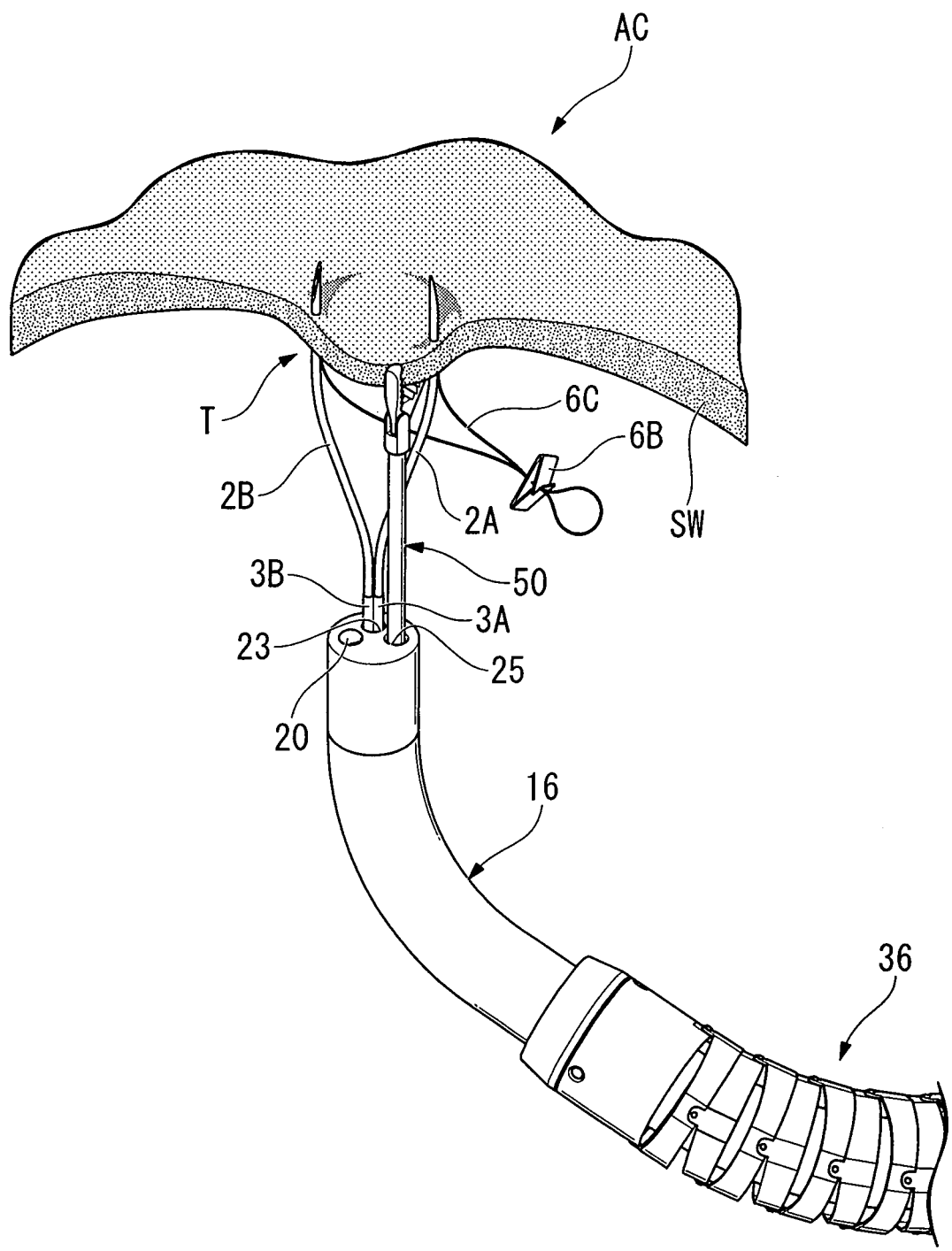
FIG. 14 is a view for describing a state of the puncture needle piercing the incision target site while retaining the double T-bars in the medical procedure according to the embodiment.

By thus advancing the needle manipulating handle 10, as shown in FIG. 14, two different locations of the stomach wall SW are simultaneously pierced.

The pusher connection part 12 is advanced from this state with respect to the needle manipulating handle 10, and the pusher 7 moves in the distal end direction of the first needle part 2A and the second needle part 2B. At this time, the anchors 6A of the double T-bars 6 are pushed by the pushers 7 to be sent out from within the first needle part 2A and the second needle part 2B to the abdominal cavity AC.

After the anchors 6A of the double T-bars 6 are released, the pusher connection part 12 retracts with respect to the needle manipulating handle 10, and moreover, the needle manipulating handle 10 retracts with respect to the sheath holding part 8, and the first needle part 2A and the second needle part 2B reenter the sheath 3. At this time, the two anchors 6A of the double T-bars 6 open in a T shape due to the bending disposition of the sutures 6C. Thereafter, the entire puncture needle 1 is pulled back to the proximal side, to be withdrawn from the treatment instrument insertion channel 23.

Figure 15:
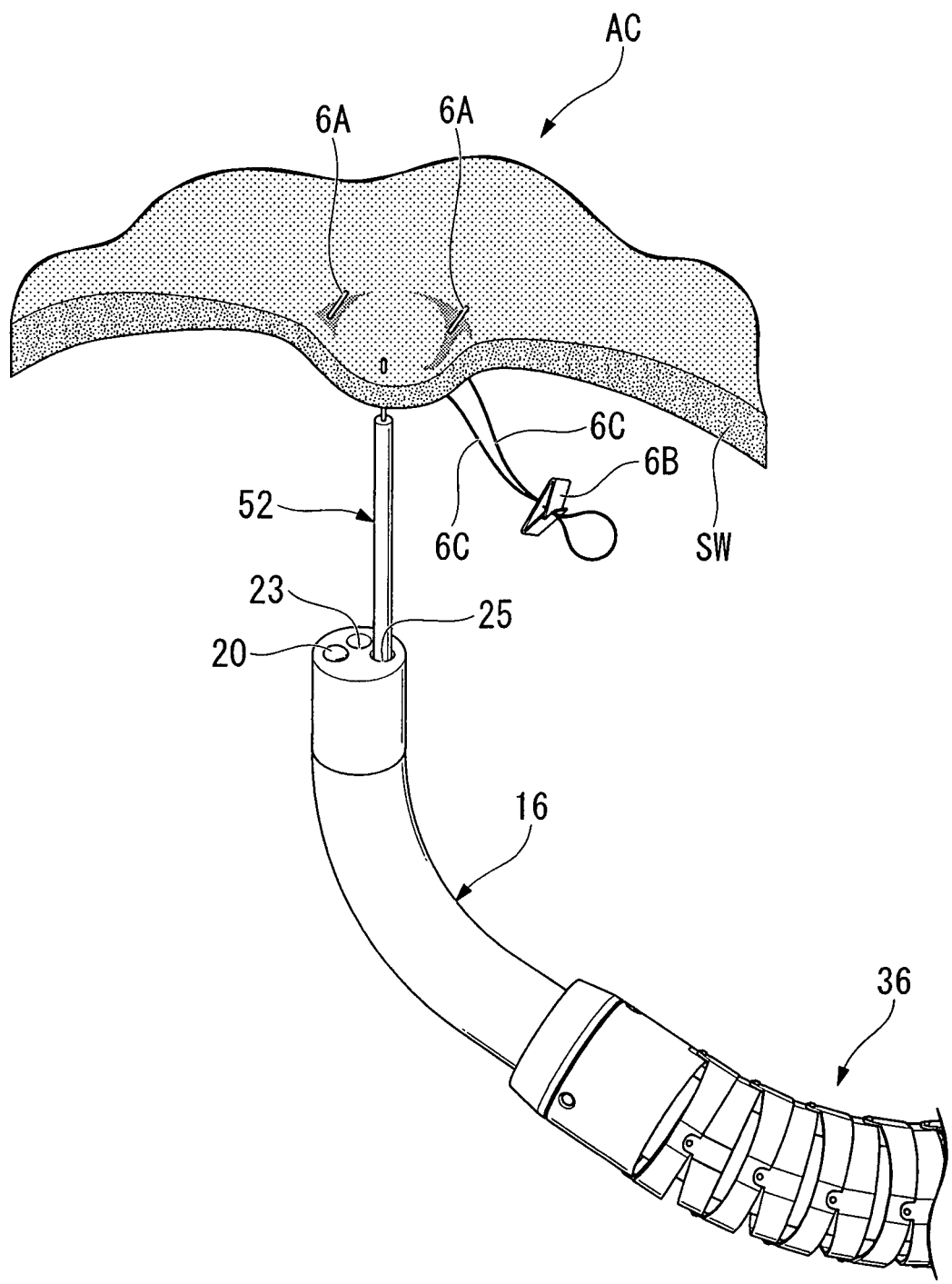
FIG. 15 is a view for describing a state releasing the anchors of the double T-bars from the puncture needle and incising the incision target site with a high-frequency knife in the medical procedure according to the embodiment.
Figure 16:
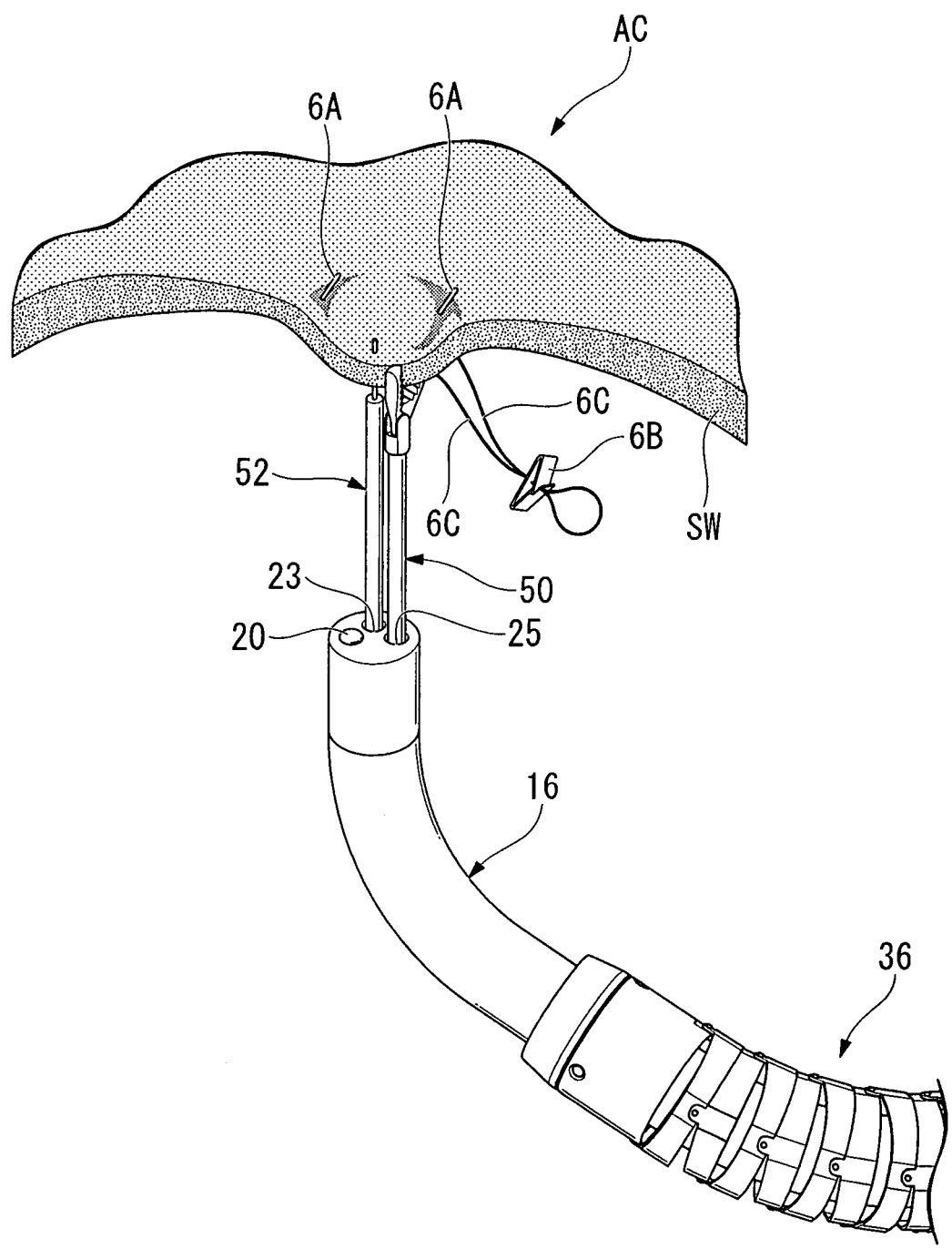
FIG. 16 is a view for describing the state of incising the incision target site while grasping it with the grasping forceps.

The process then proceeds to the incising step (S50). First, a high-frequency knife 52 is inserted through the treatment instrument insertion channel 25 instead of the grasping forceps 50. At this time, it is confirmed that the connection terminal of the power cord is connected to the connection terminal of the electrode manipulating part not shown. Then, high-frequency power is supplied from a high-frequency power source not illustrated in the state of the distal end of the high-frequency knife 52 abutting the stomach wall SW as shown in FIG. 15. As shown in FIG. 16, the high-frequency knife 52 is inserted through the treatment instrument insertion channel 23 in the state of the grasping forceps 50 inserted through the treatment instrument insertion channel 25. While pulling on the stomach wall SW with the grasping forceps 50, the distal end of the high-frequency knife 52 may be made to abut the stomach wall SW with the placement position of the double T-bars 6 and the incision position in an optimal state.

Figure 17:
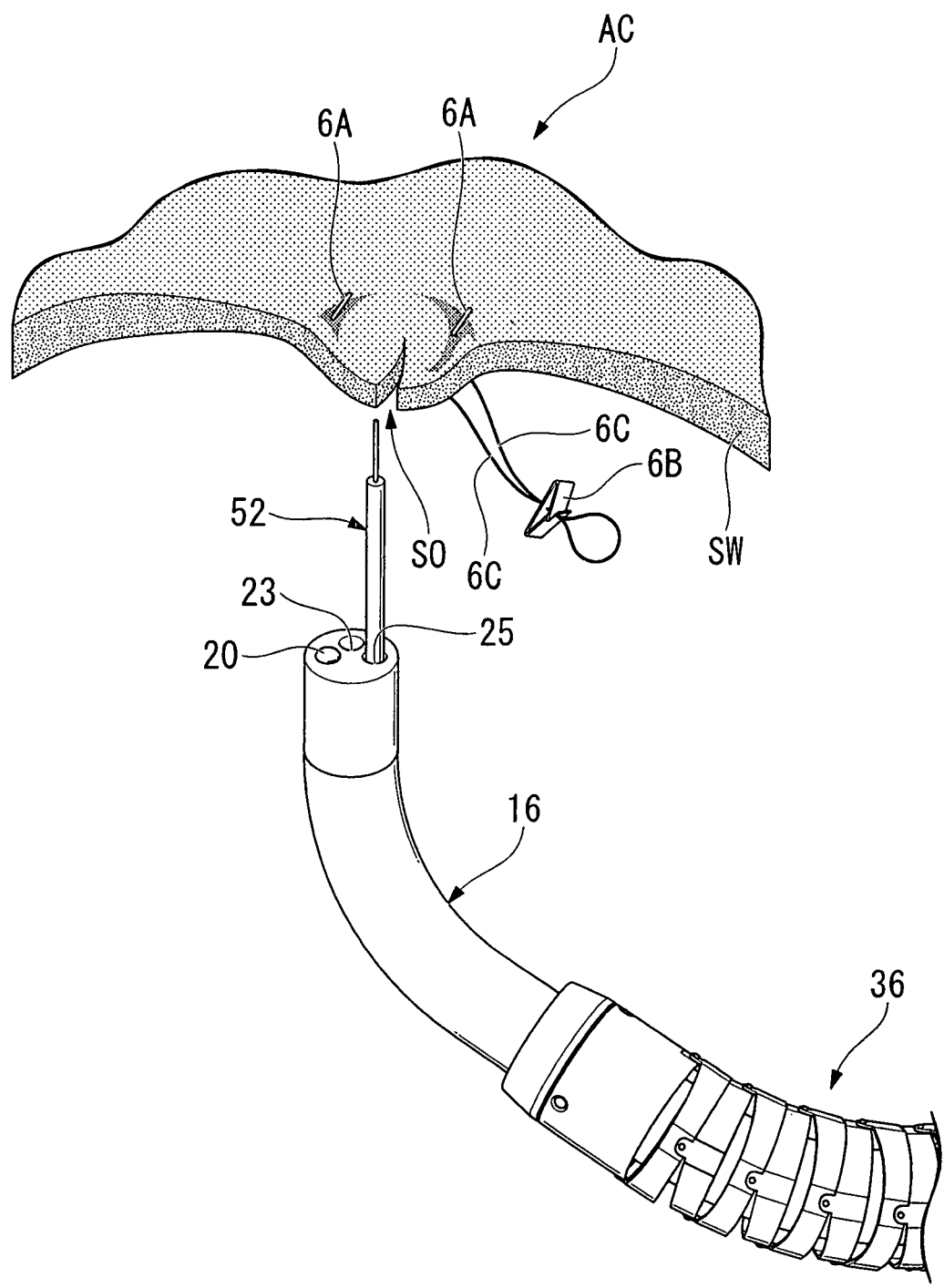
FIG. 17 is a view for describing the state of having incised the incision target site in the case of FIG. 15.
Figure 18:
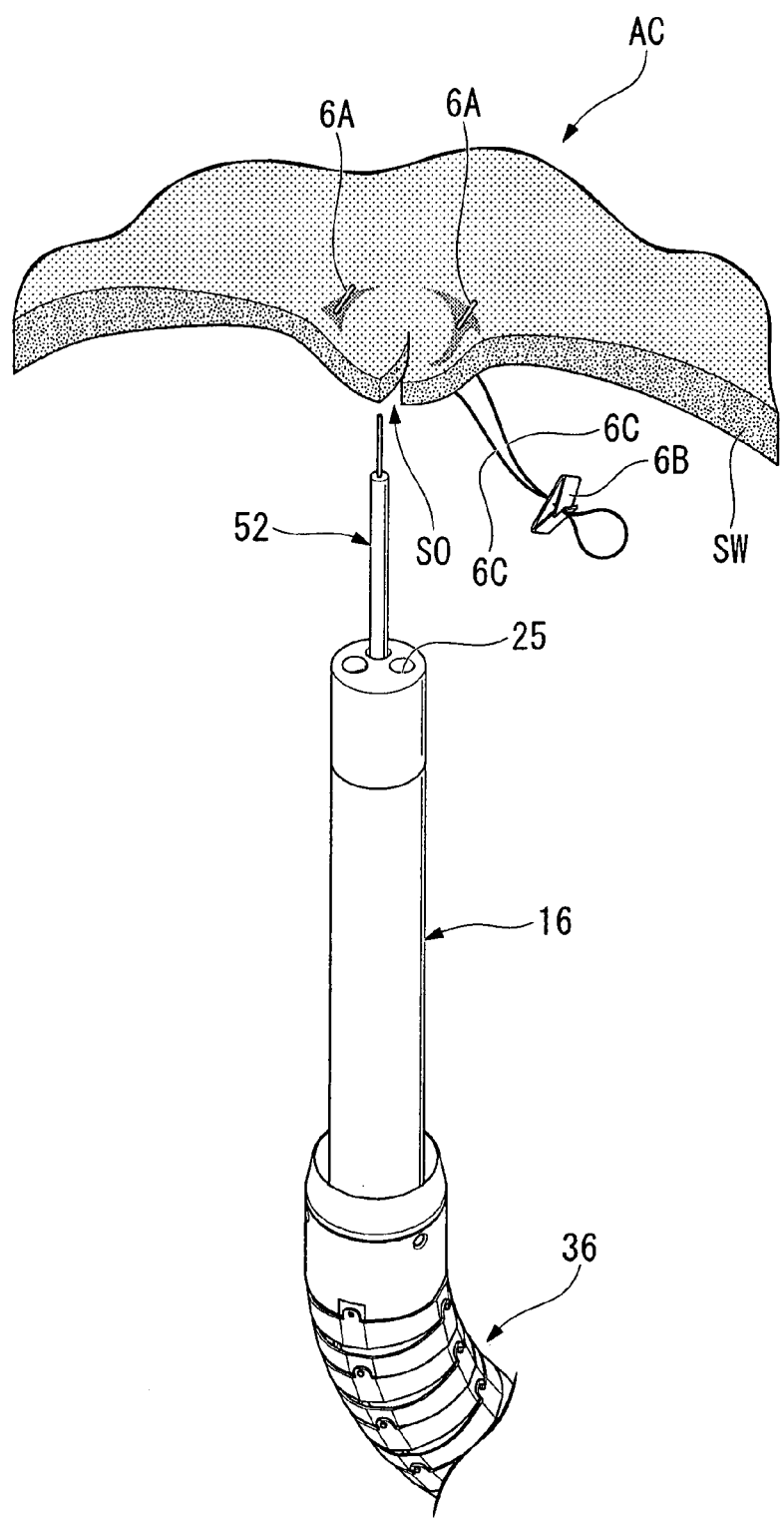
FIG. 18 is a view for describing the state of having incised the incision target site in the case of FIG. 16.

At this time, as shown in FIG. 17 and FIG. 18, the stomach wall SW is incised by the high-frequency knife 52, and an opening SO is formed in the stomach wall SW.

Figure 19:
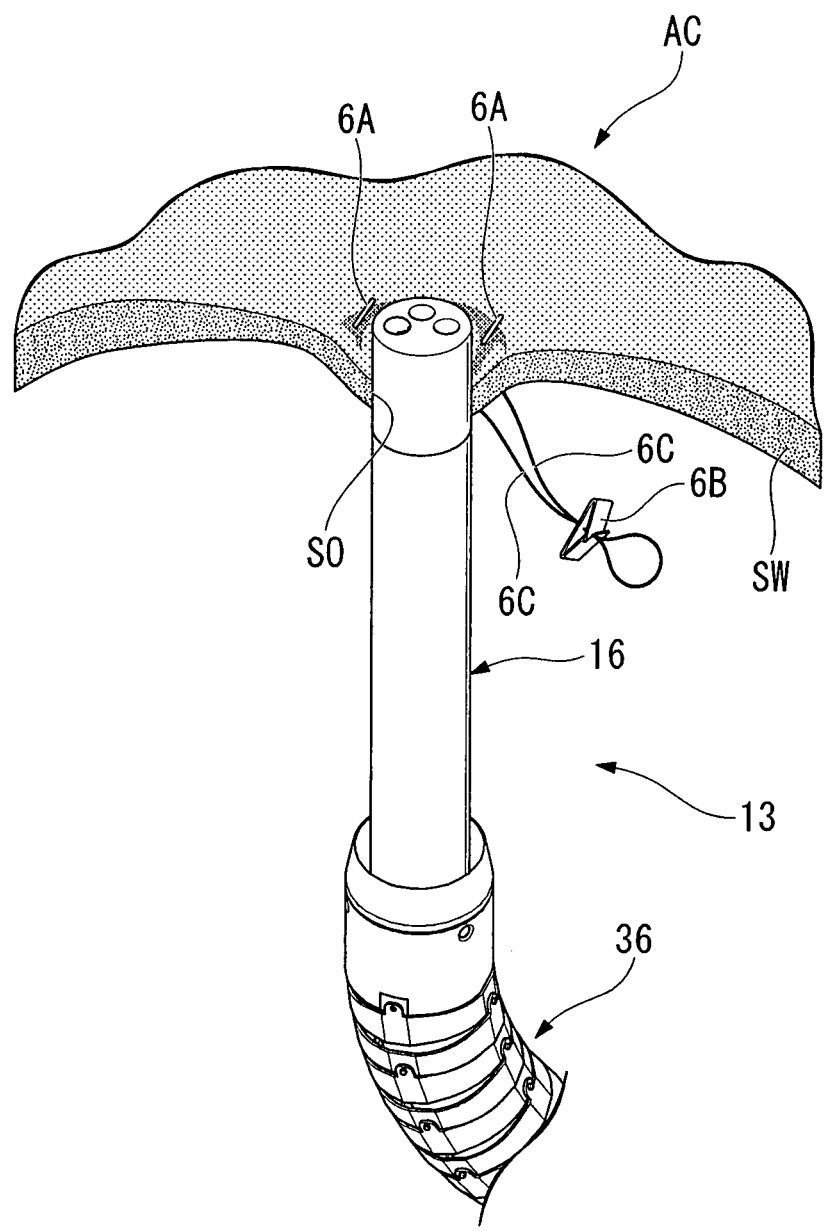
FIG. 19 is a view for describing the state of the endoscope being inserted in the abdominal cavity in the medical procedure according to the embodiment.

Next, the process proceeds to the introducing step (S60). That is, as shown in FIG. 19, after removing the high-frequency knife 52, the endoscope inserting part 16 of the endoscope 13, which is also an operative device, is introduced into the abdominal cavity AC through the opening SO. If, in this process, relative movement of the insertion part 36 and the endoscope inserting part 16 must be restricted, the endoscope lock button 47 is pressed and contacted against the endoscope inserting part 16 to fix the movement of the endoscope inserting part 16 by the frictional force. Since the endoscope lock button 47 is provided, the endoscope lock button 47 can be manipulated to restrain relative movement of the endoscope 13 with respect to the overtube 32, and the overtube 32 and the endoscope inserting part 16 can thus be inserted into the body simultaneously. Also, since the task of inserting the endoscope 13 can be performed while holding the proximal handle 44 of the overtube 32, an operation, in which the insertion part 36 of the overtube 32 is supported by one hand of the operator and the proximal handle 44 is held by the other hand, is enabled, and the operability is thus more improved.

After positioning, a treating step (S70) of performing observation, incision, cell sampling, suturing, or any of other various treatments (medical procedures) is carried out. After performing the treatment, the overtube 32 and the endoscope 13 are removed from the opening SO of the stomach wall SW.

Figure 20:
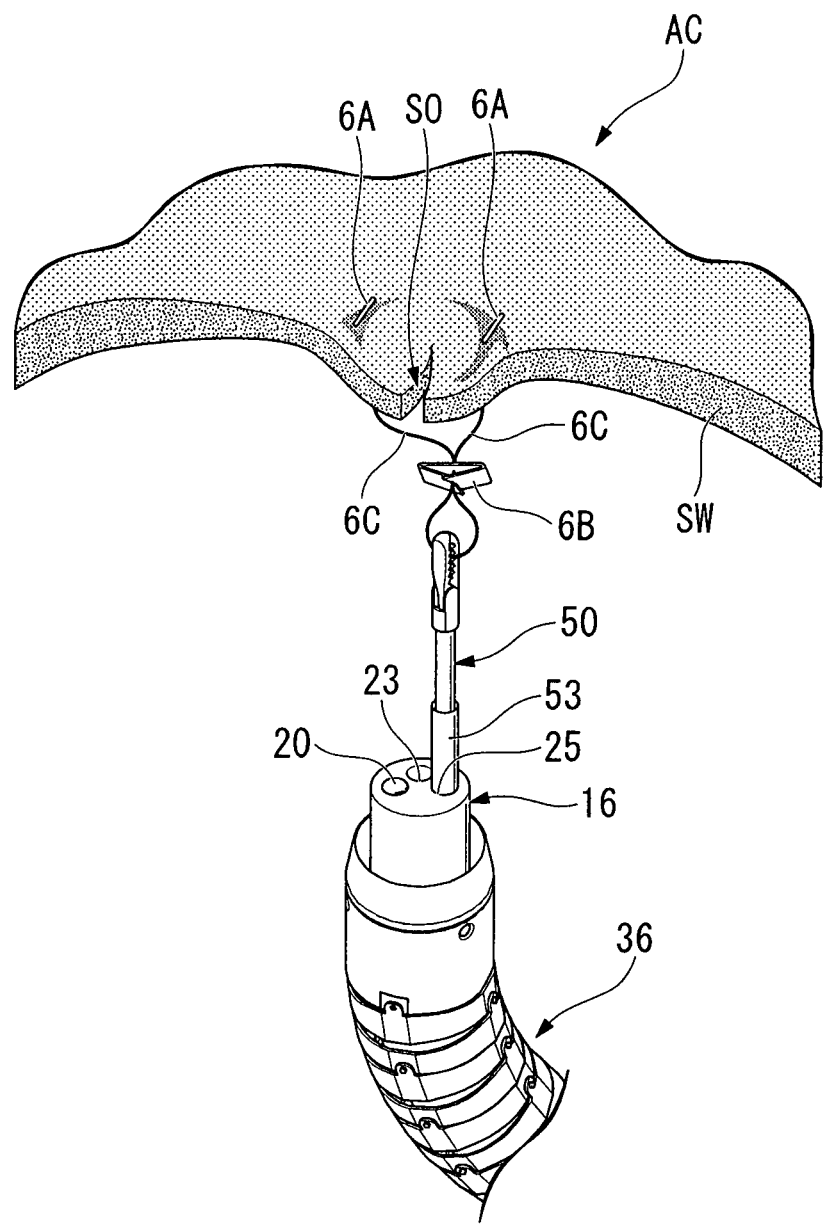
FIG. 20 is a view for describing the state of pulling and tensioning the suture of the placed double T-bars in the medical procedure according to the embodiment.
Figure 21:
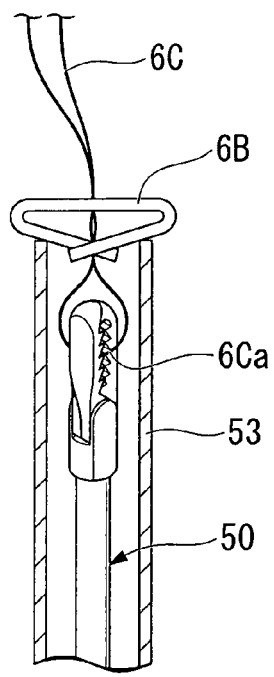
FIG. 21 is a view for describing the action in FIG. 20.
Figure 22:
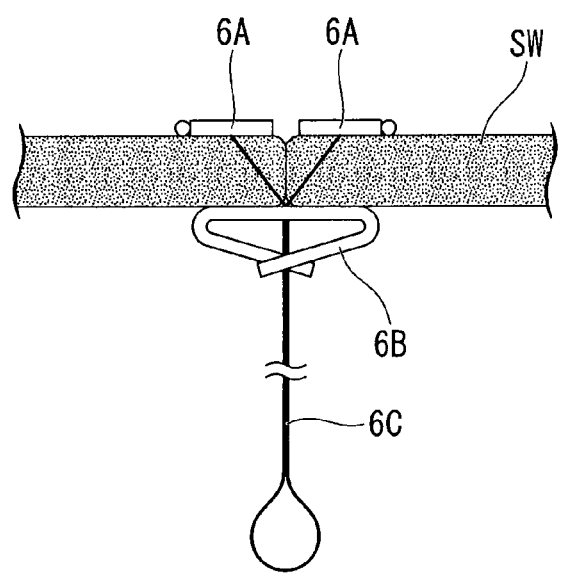
FIG. 22 is a view for describing the state of the stomach wall being bound with the double T-bars in the medical procedure according to the embodiment.

In a suturing step (S80), when removing the endoscope 13 from the opening SO, as shown in FIG. 20, the grasping forceps 50, inserted to freely advance and retract in an outer sheath 53, are protruded with the outer sheath 53 from the treatment instrument insertion channel 25. Then, as shown in FIG. 21, the large diameter part 6Ca of the sutures 6C is held and pulled by the grasping forceps 50 while making the distal end of the outer sheath 53 abut the stopper 6B of the double T-bars 6, which had been placed in advance. Thus, as shown in FIG. 22, by moving the stopper 6B to clinch the stomach wall SW, the opening SO is thereby sutured. Additional double T-bars 6, etc., are provided to perform further suturing if necessary. In this process, since the insufflation is performed in the process of placing the double T-bars 6 at the stomach wall SW, suturing by means of additional double T-bars 6 can be readily performed.

After suturing, the endoscope 13 and the overtube 32 are drawn out of the patient, the pressure applied to the abdominal cavity AC is released, and the surgical procedure is ended.

According to this puncture needle 1 and the medical procedure through a natural orifice using the puncture needle 1, since bend parts 2*a* are provided in both the first needle part 2A and the second needle part 2B, when protruding the distal end side from the bend parts 2*a* of the first needle part 2A and the second needle part 2B from the sheath 3, the gap at the distal end side of the first needle part 2A and the second needle part 2B can be made greater than the gap at the proximal end side. Accordingly, by protruding the needle part 2 from the sheath 3, the needle part 2A and the second needle part 2B can be made to simultaneously pierce living body tissue in a predetermined direction.

At this time, since an alignment part 2b is also provided in addition to the bend part 2a, when the bend part 2a and the alignment part 2b are protruded from the sheath 3, the distal ends of the first needle part 2A and the second needle part 2B can be aligned to be mutually parallel. Then, when simultaneously piercing with the first needle part 2A and the second needle part 2B, it is possible to pierce in the state of maintaining the piercing gap constant.

Also, since the sheath 3 of the puncture needle 1 is provided with the first sheath 3A and the second sheath 3B, it is possible to smoothly protrude and retract the first needle part 2A and the second needle part 2B while restricting contact between them.

The scope of the art of this invention is not restricted to the embodiments described above, and various changes can be added within a range that does not fall outside the spirit of this invention.

For example, through in the above embodiment a flexible endoscope is used as an observation device, this invention is not limited thereto and, for example, a so-called capsule endoscope may be placed inside the body, and, while observing the interior of the body using the endoscope, an insertion part of a treatment device that does not have an observation device may be inserted through the overtube to perform the desired surgical procedure.

Figure 23:
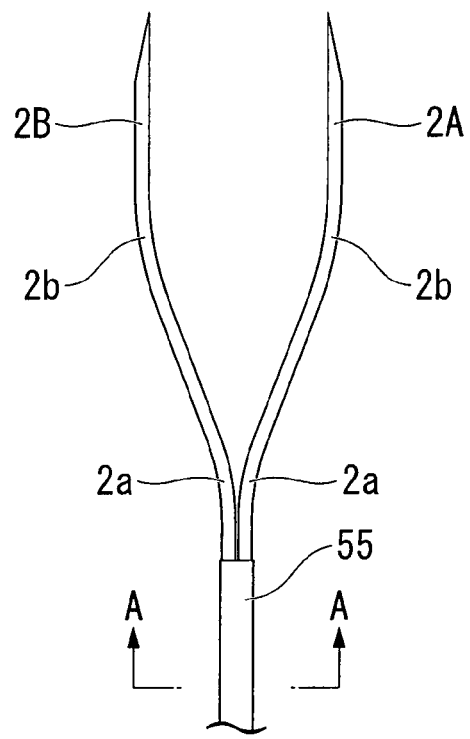
FIG. 23 is a view of the principal portions of a modification example of the puncture needle according to the one embodiment.
Figure 24:
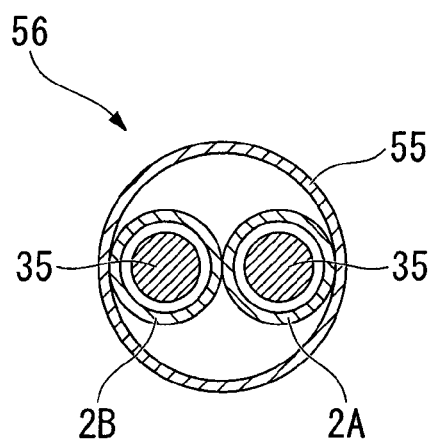
FIG. 24 is a sectional view taken along line A-A in FIG. 23.

Also, although the first needle part 2A is accommodated in the first sheath 3A and the second needle part 2B is accommodated in the second sheath 3B to freely protrude and retreat, the invention is not limited thereto. As shown in FIG. 23 and FIG. 24, it may be a puncture needle 56 in which the first needle part 2A and the second needle part 2B are accommodated in a single sheath 55. In this case, since the first needle part 2A and the second needle part 2B are accommodated in the one sheath 55, the outer diameter of the sheath 55 can be made even smaller.

Figure 25:
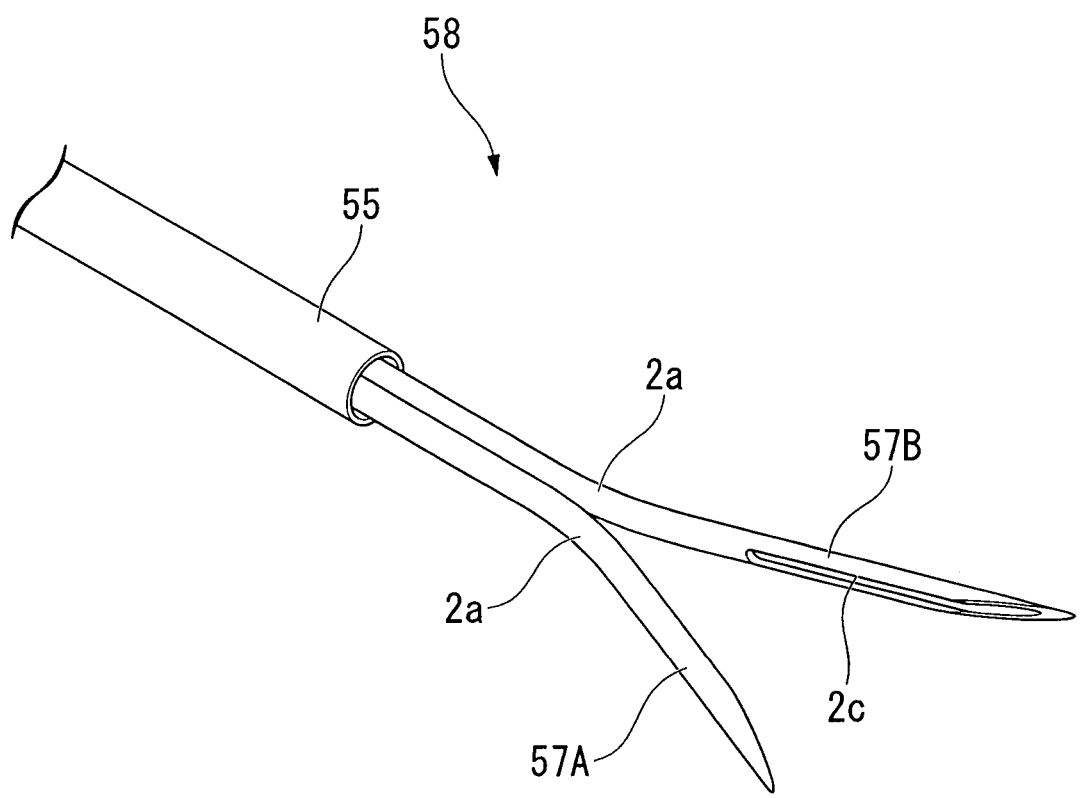
FIG. 25 is a view of the principal portions of another modification example of the puncture needle according to the one embodiment.

Moreover, as shown in FIG. 25, the puncture needle may be a puncture needle 58 in which a first needle part 57A and a second needle part 57B are provided extending toward the distal end with only the bend parts 2a provided and the alignment parts 2b not provided. In this case, the slits 2c are provided in facing side surfaces of the first needle part 57A and the second needle part 57B at the distal ends of the first needle part 57A and the second needle part 57B. Also, the distal end sides of the first needle part 57A and the second needle part 57B can be made to protrude and retreat with respect to the sheath 55, and the outer diameter of the sheath can be made still smaller.

What is claimed is:

1. A puncture needle comprising: a needle part comprising a first needle part and a second needle part that are hollow, adjacent, and have resiliency, a distal end side of the first needle part and a distal end side of the second needle part are straight and are arranged approximately parallel to each other, and a bend part that spaces the distal end sides of the first needle part and the second needle part further apart than a spacing between a proximal end side of the first needle part and a proximal end side of the second needle part is provided in at least one of the first needle part and the second needle part;
a first anchor accommodated in a distal end of the first needle part;
a second anchor accommodated in a distal end of the second needle part;
a wire member comprising a first end connected to the first anchor, a second end connected to the second anchor, a folded back portion between the first end and the second end, a first part between the first end and the folded back portion, and a second part between the second end and the folded back portion;
an outer sheath having a longitudinal axis, an interior space along the longitudinal axis, and an end face formed on an edge of an opening which is communicated with the interior space;
a stopper being slidable along the first part and the second part of the wire member and having a pressed surface which is pressed by the end face of the outer sheath;
a grasp tool being free to move in the longitudinal axial direction in the interior space of the outer sheath, having a gasping part which grasps the folded back portion, and being configured to be accommodated in the interior space with the folded back portion grasped by the grasping part; and
an operating part provided at the proximal end of the outer sheath and configured to move the outer sheath and the grasp tool relative to each other in the longitudinal axial direction; and
an incision tool capable of protruding from the distal end of the outer sheath for incising a tissue, wherein the incision tool is configured to form an opening in the tissue between a position anchored by the first anchor and a position anchored by the second anchor, in a state in which the stopper is fixed to the first part and the second part of the wire member by frictional force, and the stopper and the folded back portion are positioned away from the grasp tool and the outer sheath, wherein:
the stopper is configured to move toward the first and second parts from the folded back portion, and
when the folded back portion grasped by the grasping part and accommodated in the interior space is pulled by the grasping part with respect to the outer sheath in the direction of the proximal end of the outer sheath, the pressed surface is pressed by the end face of the outer sheath, and the stopper moves toward the first and second parts from the folded back portion to close the opening in the tissue between a position anchored by the first anchor and a position anchored by the second anchor by sliding along the first and the second part of the wire member.

2. The puncture needle according to claim 1, wherein:
alignment parts that dispose the distal end sides of the first needle part and the second needle part to be mutually parallel are provided further to the distal end side of the needle part than the bend part.

3. The puncture needle according to claim 1, wherein:
rod-like placement objects that are respectively accommodated in the first needle part and the second needle part are provided, and
the placement objects are connected by the wire member.

4. The puncture needle according to claim 3, wherein:
an axial member that presses the placement object is disposed in the first needle part and the second needle part in a manner to freely advance and retract.

5. The puncture needle according to claim 3, wherein:
the wire member passing through a slit provided at the distal end of the first needle part and a slit provided at the distal end of the second needle part.

6. The puncture needle according to claim 1, further comprising:
- an intersecting section formed by the both ends of the stopper intersecting one another so as to sandwich the wire member at the intersecting section, wherein the intersecting section closes according to the stopper moving to the folded back portion and opens according to the stopper moving to the first and second anchors so as to prevent the stopper from moving to the folded back portion and to allow the stopper to move to the first and second anchors.

7. The puncture needle according to claim 1, wherein the stopper includes a plate member having a first end and a second end in a longitudinal direction of the plate member, wherein the first end and the second end of the plate member are folded back obliquely to sandwich the wire member between the first end and the second end of the plate member.

8. The puncture needle according to claim 7 wherein the first end of the plate member is cut to a notch of triangular shape and the second end of the plate member is cut to a notch of triangular shape, and the first end and the second end of the plate members are folded back obliquely so that the notches intersect to sandwich the wire member.

9. The puncture needle according to claim 1, further comprising:
- an endoscope holding the outer sheath and the grasp tool.

\* \* \* \* \*